United States Patent [19]

Lee

[11] 4,087,441

[45] May 2, 1978

[54] PROCESS FOR PREPARING AROMATIC BISIMIDES

[75] Inventor: Chien Yung Lee, Kendall Park, N.J.

[73] Assignee: Cities Service Company, Tulsa, Okla.

[21] Appl. No.: 706,666

[22] Filed: Jul. 19, 1976

[51] Int. Cl.$^2$ .......................................... C07D 209/34
[52] U.S. Cl. .............................................. 260/326 N
[58] Field of Search .................................. 260/326 N

[56] References Cited

U.S. PATENT DOCUMENTS 3,915,930  10/1975  Dotson, Jr. et al. ............ 260/326 N

FOREIGN PATENT DOCUMENTS 1,951,632  5/1971  Germany .......................... 260/326 N
1,815,404  6/1970  Germany .......................... 260/326 N Primary Examiner—Ethel G. Love
Attorney, Agent, or Firm—Patricia J. Hogan

[57] ABSTRACT

N,N'-alkylene-bis-tetrahalophthalimides, such as N,N'-ethylene-bis-tetrabromophthalimide, are prepared by reacting about two molar proportions of a tetrahalophthalic anhydride, such as tetrabromophthalic anhydride, with one molar proportion of a diaminoalkane containing 2-6 carbon atoms, such as 1,2-diaminoethane, in an aqueous medium.

6 Claims, No Drawings

PROCESS FOR PREPARING AROMATIC BISIMIDES

BACKGROUND OF THE INVENTION

1. Field of the Invention

This invention relates to N,N'-alkylene-bis-tetrahalophthalimides and more particularly relates to an improved process for preparing them.

2. Description of the Prior Art

As taught in U.S. Pat. No. 3,873,567 (Cyba), British Pat. No. 1,287,934 (Raychem), and Sydney M. Spatz and Herman Stone, "Some N-Substituted Tetrabromophthalimide Fire-Retardant Additives," INDUSTRIAL AND ENGINEERING CHEMISTRY PRODUCT RESEARCH AND DEVELOPMENT, Volume 8, pp. 397,398 (1969), N,N'-alkylenebis-tetrahalophthalimides having utility as flame retardants can be prepared by reacting a tetrahalophthalic anhydride with a diaminoalkane in an organic solvent medium. However, since organic solvents have the disadvantages of being costly and flammable, it would be desirable to find an alternative method of preparing the compounds.

SUMMARY OF THE INVENTION

An object of this invention is to provide a novel process for preparing N,N'-alkylene-bis-tetrahalophthalimides.

Another object is to provide such a process which does not require the use of organic solvents.

These and other objects are attained by reacting about two molar proportions of a tetrahalophthalic anhydride with about one molar proportion of a diaminoalkane containing 2-6 carbon atoms in an aqueous medium.

DESCRIPTION OF THE PREFERRED EMBODIMENTS

The diaminoalkane that is reacted with the tetrahalophthalic anhydride in the practice of the invention may be any diaminoalkane containing 2-6 carbon atoms, e.g., 1,2-diaminoethane, 1,2-diaminopropane, 1,3-diaminopropane, 1,4-diaminobutane, 1,5-diaminopentane, 1,6-diaminohexane, etc. However, it is preferably 1,2-diaminoethane.

The tetrahalophthalic anhydride is usually tetrabromo- or tetrachlorophthalic anhydride and is preferably tetrabromophthalic anhydride.

The water that is employed as a reaction medium in the practice of the invention may be used in any suitable amount, usually an amount such as to provide a solids content of about 5-50%, preferably about 20-30%, by weight.

Except for the essential aspects mentioned above, i.e., the use of water as the reaction medium and the use of a particular ratio of reactants, the manner of reacting the tetrahalophthalic anhydride with the diaminoalkane is not critical. The reaction can be conducted by conventional techniques. However, it is advantageous to conduct the reaction by (1) dispersing the anhydride in water, (2) heating the dispersion, (3) adding the diaminoalkane gradually, e.g., over a period of about 0.25–4 hours, and (4) continuing to heat the reaction mixture for at least about 30 minutes, frequently for about 30 minutes to 2 hours. The reaction temperature is advantageously in the range of about 20°–200° C., preferably about 80°–150° C.; and super-atmospheric pressures may be employed when required to prevent boiling. The product may then be recovered by conventional cooling and filtering techniques, and it is then dried at about 150°–300° C., usually about 150°–200° C.

The process of the invention is particularly advantageous in that it provides a method of preparing N,N'-alkylene-bis-tetrahalophthalimides without the use of costly and flammable organic solvents. The products, like the N,N'-alkylene-bis-tetrahalophthalimides of the prior art, are particularly useful as flame retardants.

The following example is given to illustrate the invention and is not intended as a limitation thereof.

EXAMPLE

Charge 500 g. of water and 47 g. of tetrabromophthalic anhydride to a suitable reaction vessel. Heat the mixture to about 130°–140° C., and add a solution of 3 g. of 1,2-diaminoethane in 20 g. of water over a period of about one hour. Maintain the reaction temperature of about 130°–140° C. for an additional four hours. Then cool the reaction mixture to about 40° C., filter, and dry the product at about 200° C. The product is N,N'-ethylene-bis-tetrabromophthalimide, as confirmed by an infra-red spectrum.

Similar results are observed when the tetrabromophthalic anhydride and 1,2-diaminoethane are replaced by materials taught to be their equivalents in the specification.

It is obvious that many variations may be made in the products and processes set forth above without departing from the spirit and scope of this invention.

What is claimed is:

1. A process for preparing an N,N'-alkylene-bis-tetrahalophthalimide which comprises reacting about two molar proportions of a tetrahalophthalic anhydride with about one molar proportion of a diaminoalkane containing 2-6 carbon atoms in an aqueous medium consisting essentially of sufficient water to provide a solids content of about 5–50% by weight, (2) recovering the solid product of the reaction, and (3) drying the product at about 150°–300° C.

2. The process of claim 1 wherein the tetrahalophthalic anhydride is tetrabromophthalic anhydride.

3. The process of claim 1 wherein the diaminoalkane is 1,2-diaminoethane.

4. The process of claim 1 wherein the reaction is conducted at a temperature in the range of about 20°–200° C.

5. The process of claim 4 wherein the temperature is about 80°–150° C.

6. The process of claim 1 wherein the aqueous medium is employed in an amount such as to provide a solids content of about 20–30% by weight.

* * * * *